United States Patent [19]

Levos et al.

[11] 4,450,730
[45] May 29, 1984

[54] LIQUID SAMPLER WHEREIN SOLUTION TO BE SAMPLED IS USED AS RETRIEVABLE SAMPLER WASH

[75] Inventors: Christian Levos, Martinvast; Daniel Perie, Cherbourg; Jean-Francois Gex, Haineville, all of France

[73] Assignee: Commissariat a l'Energie Atomique, Paris, France

[21] Appl. No.: 365,004

[22] Filed: Apr. 2, 1982

[30] Foreign Application Priority Data

Apr. 8, 1981 [FR] France .............................. 81 07064

[51] Int. Cl.³ .......................... G01N 1/12; G01N 1/14
[52] U.S. Cl. ............................. 73/864.61; 73/864.35
[58] Field of Search ............... 73/864.35, 864.34, 864, 73/863, 864.61

[56] References Cited

U.S. PATENT DOCUMENTS

| | | | |
|---|---|---|---|
| 3,492,946 | 2/1970 | Martin | 73/864.34 X |
| 3,896,673 | 7/1975 | Adouze et al. | 72/864.34 X |
| 4,213,342 | 7/1980 | Gates | 73/864.61 X |

FOREIGN PATENT DOCUMENTS

| | | | |
|---|---|---|---|
| 2642065 | 12/1977 | Fed. Rep. of Germany | 73/864.35 |
| 2824153 | 12/1979 | Fed. Rep. of Germany | 73/864.35 |
| 1247657 | 10/1960 | France | 73/864.35 |
| 2347671 | 11/1977 | France | 73/864.35 |
| 878504 | 10/1961 | United Kingdom | 73/864.35 |

*Primary Examiner*—Gerald Goldberg
*Assistant Examiner*—Tom Noland
*Attorney, Agent, or Firm*—James E. Nilles

[57] ABSTRACT

Apparatus for drawing a sample of liquid from a body thereof into a sample bottle that has a pierceable resilient sealing closure at one of its ends comprises a support that holds the sample bottle with that end lowermost and at an elevation above the body. Two hollow needles project up from the support to pierce the closure and have their pointed upper ends in the interior of the sample bottle. A shorter one of the two needles is connected with a first duct that extends down to below the surface of liquid in the body; the other needle is communicated with the interior of a sealed wash bottle, near its bottom, which is a little below the support. Another duct, opening from the interior of the wash bottle, near its top, is connectable to a suction source, for drawing liquid through the first duct and the sample bottle into the wash bottle, thus ensuring that liquid remaining in the sample bottle is representative. When that other duct is opened to atmosphere, liquid is siphoned from the wash bottle, through a filled sample bottle, back to the body.

3 Claims, 2 Drawing Figures

LIQUID SAMPLER WHEREIN SOLUTION TO BE SAMPLED IS USED AS RETRIEVABLE SAMPLER WASH

BACKGROUND OF THE INVENTION

The present invention relates to an apparatus for taking liquid samples and more particularly radioactive liquids for analysis.

Most existing processes use a sampling bottle sealed by a flexible diaphragm in which a vacuum has previously been produced. This bottle is turned over and its upper end is punctured with a hollow needle, whose lower end is immersed in the tank containing the liquid to be sampled and the liquid rises up into the bottle by suction. The lower end of the hollow needle may optionally be immersed in an intermediate tank, which can be filled and emptied by a vacuum-producing system. Such installations generally have a larger number of sampling points (up to 19) arranged in a circular manner and under the control of a hydraulic control member.

These installations have a certain number of disadvantages. First, their cost price is high, due to the advanced mechanization for a limited number of sampling operations. Furthermore, after each sampling operation, traces of the analysed liquid are left behind within the hollow needle and this residual liquid does not develop in the same way as the liquid contained in the tank. In the prior art apparatuses, it is not possible to rinse the needle and during a following analysis, there is a risk that the liquid contained in the tank will be contaminated by the traces left behind within the hollow needle during the preceding analysis. Thus, the sample collected in the bottle is not representative.

BRIEF SUMMARY OF THE INVENTION

The object of the present invention is to provide a sampling apparatus which does not have these disadvantages, can be easily used for a small number of sampling operations, obviates the necessity of forming a vacuum in the sampling bottles and permits the hollow needles to be rinsed.

According to the main feature of the apparatus according to the invention, it comprises means for supporting a sampling bottle tightly sealed by a stopper or flexible diaphragm, connecting means linking the bottle on the one hand to a tank containing the liquid to be sampled and on the other hand to a second bottle, called the wash bottle, said connecting means comprising a first hollow needle connecting the sampling bottle to the liquid to be sampled via a pipe and a second hollow needle connecting the sampling bottle to the wash bottle via another pipe, the first hollow needle issuing into the sampling bottle at a level below that at which issues the second hollow needle, and comprising means making it possible to produce a pressure difference between the tank and the wash bottle.

According to another feature of the apparatus according to the invention, the means enabling a pressure difference to be produced between the tank and the wash bottle comprise a pipe connecting the latter to a suction system, said pipe being provided with a sealing or closing device.

According to a third feature of the apparatus according to the invention, the lower part of the wash bottle is at a higher level than the upper part of the tank containing the liquid to be sampled.

It is immediately apparent that as a result of the apparatus according to the invention, it is no longer necessary to produce a vacuum beforehand in the sampling bottle and that, in addition, the suction system permits "continuous" operation. This continuous operation brings about a prior rinsing of the pipes and needles and consequently the taking of a representative sample.

BRIEF DESCRIPTION OF THE DRAWINGS

The invention is described in greater detail hereinafter relative to non-limitative embodiments and the attached drawings, wherein.

DETAILED DESCRIPTION OF THE PREFERRED EMBODIMENTS

Figure 1:
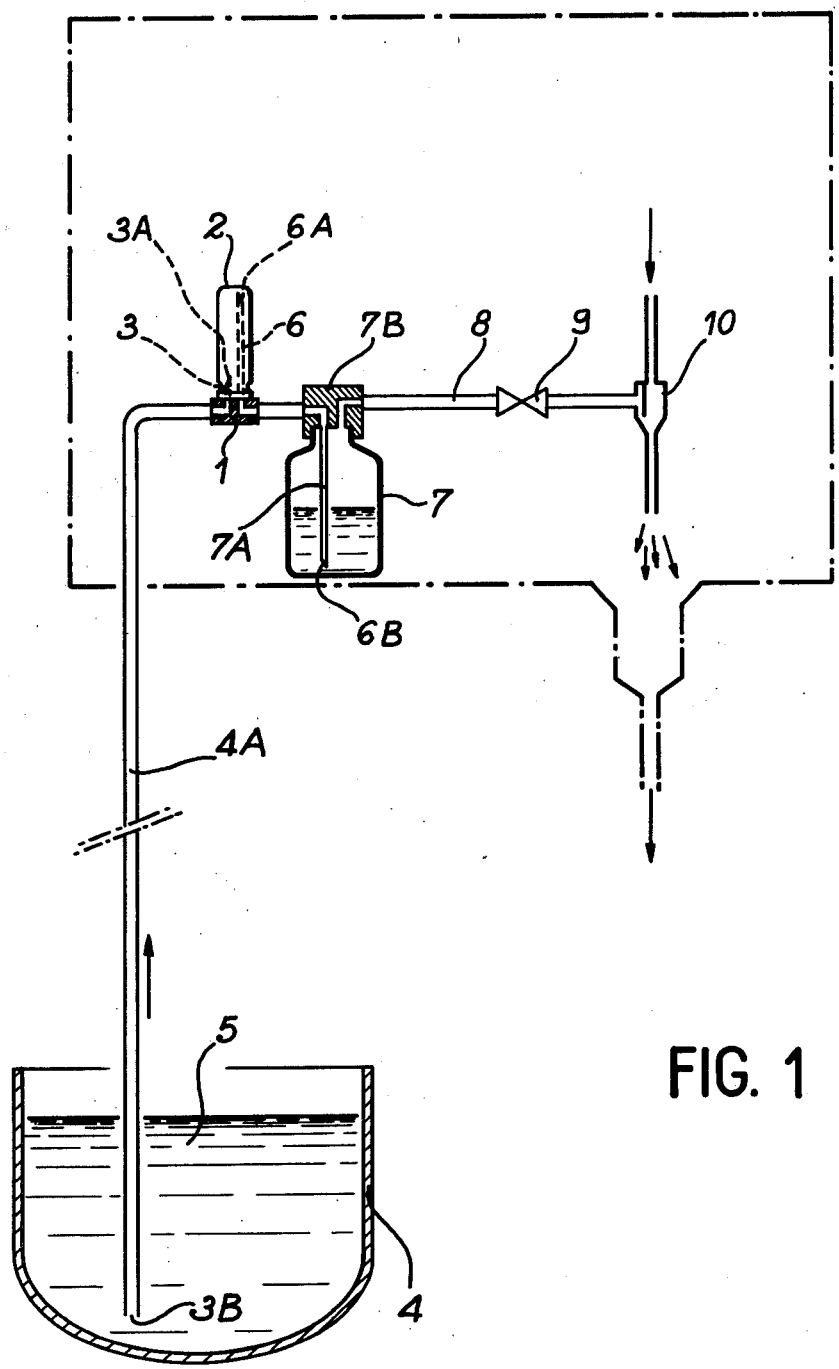
FIG. 1 is a diagrammatic sectional view of the apparatus according to the invention.

FIG. 1 shows the complete apparatus according to the invention, which comprises a support 1 on which is placed the sampling bottle 2. Projecting up from support 1 is a first hollow needle 3, whose upper end enters the sampling bottle 2. The first hollow needle 3 is connected with one end of a pipe 4a, whose other end 3b is immersed in a tank 4 containing the liquid 5 to be sampled. A second hollow needle 6 also projects up from support 1 to have an upper end 6a issuing into bottle 2. It is connected to one end of a pipe 7a, which passes through a device 7b tightly seals the upper part of a second bottle, called the wash bottle 7. The other end 6b of pipe 7a opens out into the bottom of the second bottle. The capacity of wash bottle 7 is greater than that of the sampling bottle 2. The interior of bottle 7 is communicated via device 7b to a pipe 8 which is provided with a sealing or closure system 9, e.g. a valve, and which leads to a suction system 10. The latter can be a water jet pump or an air ejector making it possible to produce a pressure difference between tank 4 and wash bottle 7.

Figure 2:
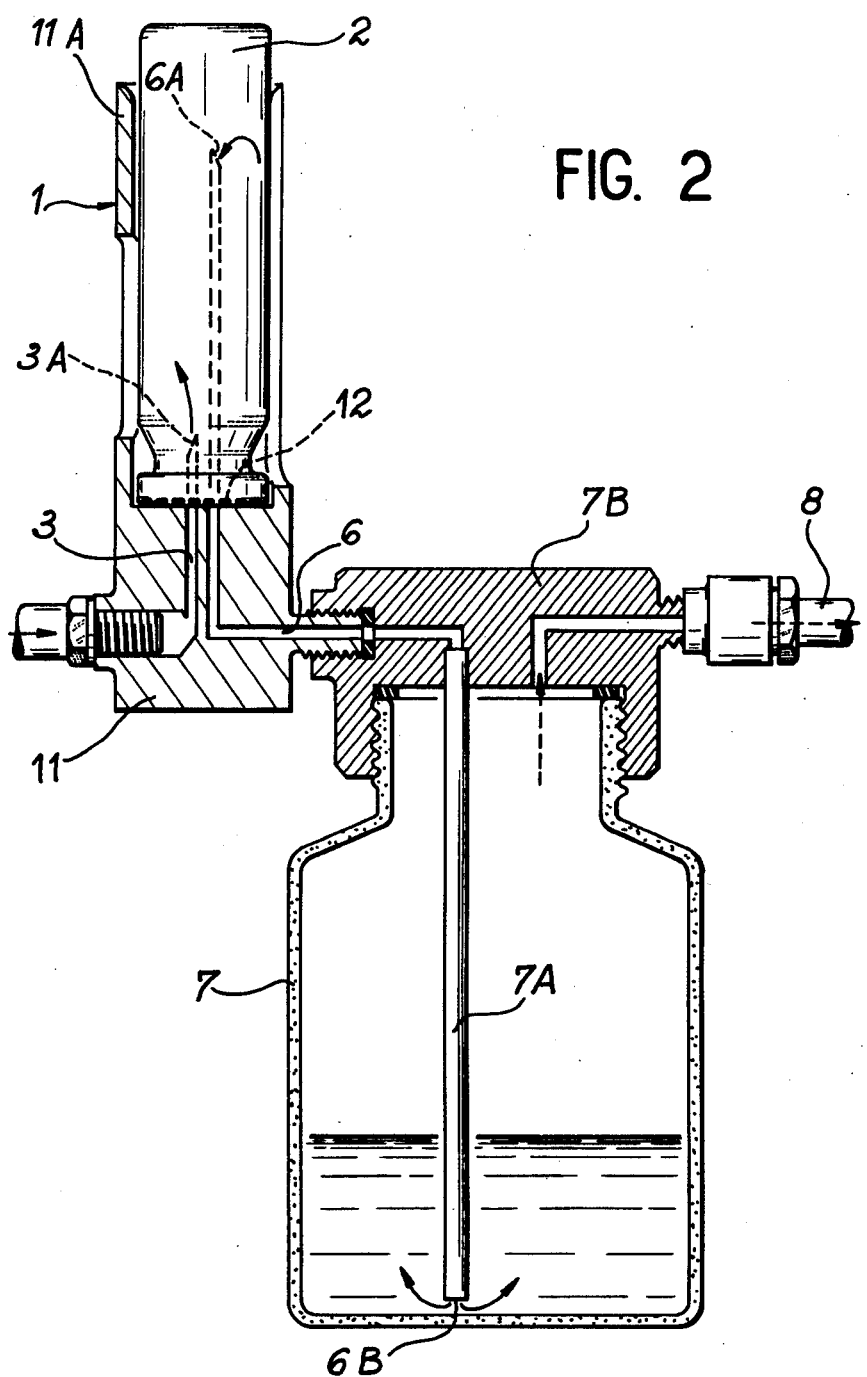
FIG. 2 is a larger scale, diagrammatic, sectional view showing in more detailed manner the sampling bottle and the wash bottle.

FIG. 2 shows in greater detail the apparatus used as a support for the sampling bottle 2. Support 1 has a solid or unbroken lower part 11 through which pass the two hollow needles 3 and 6. The latter issue into the inside of a hollow cylindrical part 11a that comprises an upward extension of the lower part 11. The sampling bottle, tightly sealed by a stopper or flexible diaphragm 12, is introduced into the hollow cylindrical part 11a. Bottle 2 is turned over in such a way that during this operation, diaphragm 12 is perforated by the two needles 3 and 6. The walls of the hollow cylindrical part 11a are opertured to such an extent that it is possible to check the level of the liquid within bottle 2.

The apparatus functions in the following manner. On placing the sampling bottle 2 on support 1 and with wash bottle 7 empty, valve 9 is opened and the suction system 10 is started up. This produces an underpressure within wash bottle 7 and, by suction, the liquid 5 contained in tank 4 rises along pipe 4a and needle 3 up to sampling bottle 2. Obviously, for this to be possible, it is necessary for the wash bottle 7 and sampling bottle 2 to be at a level above that of the upper part of tank 4. It must also be ensured that the liquid height difference between tank 4 and wash bottle 7 represents a pressure difference below the vacuum produced by the water jet pump. Inside bottle 2, end 3a of needle 3 is at a level below that of end 6a of needle 6. This arrangement is necessary to ensure that the liquid to be analysed and arriving via needle 3 at least partly fills the sampling bottle 2 before flowing out into wash bottle 7 through needle 6 and pipe 7a.

Wash bottle 7 is used because it is necessary to draw through bottle 2 a quantity of liquid equal to several times the capacity of that bottle in order to have a representative sample. Thus, even in the case of the apparatus according to the invention, traces of liquid are left in needle 3 and pipe 4a after analysis, so that they must be rinsed before the following analysis. In a specific example where the height difference between tank 5 and wash bottle 7 is 6.50 m and the capacity of sampling bottle 2 is 10 ml, a representative sample can only be obtained by replenishing the content of the sampling bottle at least 10 times. The wash bottle 7 is used for storing the overflow from this operation.

Once bottle 2 is filled with a representative sample, valve 9 is closed and the water jet pump 10 stopped.

Bottle 2 is then removed and is replaced by an empty bottle. During the time between the removal of the first bottle and the fitting of the second, the liquid quantities in needle 3 and pipe 4a on the one hand and needle 6 and pipe 7a on the other drop again by gravity into tank 4 and bottle 7 respectively.

The following procedure is adopted to recover the liquid in bottle 7 and recycle it into tank 4. Firstly, the circuit is restarted by opening valve 9 and starting up the water jet pump 10 until the new sampling bottle is filled with liquid. The water jet pump 10 is then stopped, but the valve 9 is not closed. The surface of the liquid contained in wash bottle 7 is then exposed to atmospheric pressure in the same way as liquid 5 in tank 4. As the surface of the liquid in bottle 7 is at a higher level than that of the surface of liquid 5, and as bottle 2 is filled with liquid between ends 3a and 6a of needles 3 and 6, a siphoning phenomenon occurs and all the liquid contained in bottle 7 automatically drops back into tank 4. For this to be possible, it is obvious that pipe 7a must enter bottle 7 at the lowest possible level. The apparatus is then ready to start a new sampling operation.

The apparatus according to the invention has numerous advantages and firstly a high degree of simplicity, because it does not involve the use of any automatic equipment or vacuum regulation system. The various components constituting the apparatus are inexpensive and are readily commercially available. Moreover, the distance between the apparatus and the tank is unimportant, because it is merely necessary for the difference in level between the wash bottle and the tank for the liquid to be sampled to represent a pressure difference lower than the vacuum produced by the water jet pump. Thus, an apparatus according to the invention is able to function with a level difference of 7.50 m and a pipe length of 80 m. Moreover, the liquid overflow collected in bottle 7 during the rinsing of needle 3 can easily be returned to tank 4 by siphoning following each sampling operation. Thus, the danger of transferring radioactive effluents or effluents containing fissile materials into the water jet pump circuit or into the atmosphere when an air ejector is used is eliminated. The second bottle used for the siphoning can be left in place for the following analysis, if there is no risk of the solution crystallizing over a period of time.

The invention is obviously not limited to the single embodiment described hereinbefore and in fact covers all variants thereof.

What is claimed is:

1. Apparatus whereby a sample can be drawn from a body of liquid that is maintained substantially at a predetermined level into a sample bottle that has at one end thereof a resilient pierceable sealing closure, said apparatus comprising:
   A. supporting means for receiving and holding the sample bottle with its said end lowermost and at an elevation substantially above said level;
   B. a pair of upwardly projecting hollow needles on said supporting means, each of which has a pointed upper end that pierces the closure of the sample bottle received on said supporting means to enter the interior of that sample bottle, the upper end of one of said hollow needles being a substantial distance below the upper end of the other;
   C. a first duct having one end immersible in said body of liquid to be below said level and having its other end communicated with said one hollow needle;
   D. a sealed wash bottle having a bottom end below said elevation but substantially above said level;
   E. a second duct having one end opening to the interior of said wash bottle near an upper end thereof and having its other end connectable with a suction source; and
   F. a third duct having one end communicated with said other hollow needle and having its other end opening to the interior of the wash bottle near the bottom end thereof, so that upon connection of said second duct with said suction source a substantial quantity of liquid from said body is drawn into the wash bottle through the first duct and the sample bottle on said supporting means, to ensure that liquid retained in the sample bottle is representative of liquid in said body.

2. The apparatus of claim 1 wherein said wash bottle has a capacity that is on the order of ten times the capacity of the sample bottle to be received on said supporting means.

3. The apparatus of claim 1, wherein said second duct has its said other end alternatively and selectably connectable with said suction source and with the atmosphere, to enable liquid in the wash bottle to be siphoned back to said body through the sample bottle when filled and on said supporting means.

* * * * *